United States Patent [19]
Sahley

[11] Patent Number: 5,681,578
[45] Date of Patent: Oct. 28, 1997

[54] COMPOSITION FOR RELIEVING STRESS ANXIETY, GRIEF, AND DEPRESSION

[76] Inventor: Billie J. Sahley, 5426 King Albert, San Antonio, Tex. 78229

[21] Appl. No.: 589,757

[22] Filed: Jan. 22, 1996

[51] Int. Cl.⁶ ...................................................... A61K 9/48
[52] U.S. Cl. .................... 424/439; 424/195.1; 424/451; 424/639; 424/641; 424/643; 424/655; 424/678; 424/681; 424/682; 514/168; 514/188; 514/458; 514/474; 514/566; 514/725; 514/810; 514/812; 514/813; 514/904; 514/905
[58] Field of Search .................... 424/439, 195.1, 424/451, 639, 641, 643, 655, 678, 681, 682; 514/168, 188, 458, 474, 566, 725, 810, 812, 813, 904, 905

[56] References Cited

U.S. PATENT DOCUMENTS 5,051,258   9/1991   Sahley ...................................... 424/439

OTHER PUBLICATIONS

Chemical Abstracts 1987: 509350 (1987) (Wilmon et al).

Derwent (WPIDS) Abstract 94–227296 (Le, et al, Corresponds to DE 440 3157, 1994.

*Primary Examiner*—Marianne M. Cintins
*Assistant Examiner*—Keith MacMillan
*Attorney, Agent, or Firm*—Donald R. Comuzzi; Christopher L. Makay

[57] ABSTRACT

A composition for relieving stress, anxiety, grief, and depression includes GABA (gamma amino butyric acid), glutamine, glycine, magnesium, passion flower, primula officinalis, and vitamin B-6.

10 Claims, No Drawings

COMPOSITION FOR RELIEVING STRESS ANXIETY, GRIEF, AND DEPRESSION

BACKGROUND OF THE INVENTION

1. Field of the Invention

The present invention relates to a composition of matter for enhancing the body's ability to cope with stress, anxiety, grief, and depression and, more particularly, but not by way of limitation, to a compositional blend of amino acids, herbs, and vitamin B-6 that reduces stress, anxiety, grief, and depression by aiding the natural inhibitory neurotransmitter system of the brain.

2. Description of the Related Art

The brain controls the human body and is responsible for every thought, sensation, behavior, and memory. For the brain to control the human body, its individual cells must be in constant communication. That communication occurs through the release of neurotransmitters at the synapse between two neurons of individual brain cells. Neurotransmitters chemically transmit necessary information such as emotional responses, pain sensations, and voluntary muscle movements. Furthermore, certain neurotransmitters are inhibitory and actually prevent responses such as the emotional ones of anxiety and/or grief. Thus, neurotransmitters are essential to the mental, emotional, and physical well being of any person because, without sufficient levels, the brain cells do not properly communicate.

Although neurotransmitters are extremely important, few people receive sufficient amounts of the nutrients necessary to stimulate proper neurotransmitter production. Thus, if a person experiences stress, anxiety, grief, and/or depression, associated mental and emotional responses are magnified, particularly when certain inhibitory neurotransmitters are deficient. Current treatments for the above conditions, which consist primarily of prescription drugs, only provide temporary relief and often exacerbate the problem. Prescription drugs either stimulate the excessive release of pre-existing neurotransmitters or serve as a substitute for them. That excessive release or substitution relieves the condition, however, such relief is only temporary because, once the drug wears off, the condition returns. Furthermore, excessive release of neurotransmitters often produces a more acute condition because it depletes available neurotransmitters without satisfactory replenishment. Thus, prescription drugs, which only temporarily relieve the condition without providing a lasting cure, often facilitate a chronic condition requiring prolonged drug use.

Prescription drugs are therefore not the answer to the problems of stress, anxiety, grief, and/or depression. Accordingly, a treatment that relieves stress, anxiety, grief, and/or depression by enhancing the natural inhibitory neurotransmitter system of the brain would greatly benefit sufferers of those conditions.

SUMMARY OF THE INVENTION

In accordance with the present invention, a composition for relieving stress, anxiety, grief, and depression includes GABA (gamma amino butyric acid) from about 33.3% to about 43.0% total composition weight, glutamine from about 11.4% to about 15.2% total composition weight, glycine from about 7.6% to about 11.4% total composition weight, magnesium from about 7.6% to about 11.4% total composition weight, passion flower from about 12.4% to about 16.2% total composition weight, primula officinalis from about 12.4% to about 16.2% total composition weight, and vitamin B-6 from about 0.7% to about 1.2% total composition weight.

DETAILED DESCRIPTION OF THE PREFERRED EMBODIMENT

A compositional blend that relieves stress, anxiety, grief, and/or depression by enhancing the natural inhibitory neurotransmitter system of the brain includes GABA (gamma amino butyric acid), glutamine, glycine, magnesium, passion flower, primula officinalis, and vitamin B-6. In this preferred embodiment, the compositional blend of GABA, glutamine, glycine, magnesium, passion flower, primula officinalis, and vitamin B-6 is capsulized for distribution using any of several well known processes such as those practiced by Metabolic Maintenance Products, Inc. which has a place of business at 68994 North Pine Street, Sisters, Oreg. 97759.

The compositional blend is capsulized by percent total weight as follows:

| | |
|---|---|
| GABA | from about 33.3% to about 43.0% |
| Glutamine | from about 11.4% to about 15.2% |
| Glycine | from about 7.6% to about 11.4% |
| Magnesium | from about 7.6% to about 11.4% |
| Passion Flower | from about 12.4% to about 16.2% |
| *Primula officinalis* | from about 12.4% to about 16.2% |
| Vitamin B-6 | from about 0.7% to about 1.2% |

As previously described, the compositional blend is placed into capsules so that four capsules, which would be the recommended daily dose for a child at least four years of age or an adult, will contain the following:

| | | USRDA* |
|---|---|---|
| GABA | 800 mg | ** |
| Glutamine | 280 mg | ** |
| Glycine | 200 mg | ** |
| Magnesium | 200 mg | 57% |
| Passion Flower | 300 mg | ** |
| *Primula officinalis* | 300 mg | ** |
| Vitamin B-6 | 20 mg | 1000% |

*Percent U.S. Recommended Daily Allowance for adults and children four or more years of age.
**No U.S. Recommended Daily allowance established.

The compositional blend includes GABA, glutamine, and glycine because they are amino acids that form the major inhibitory neurotransmitters of the brain. A person experiencing stress, anxiety, grief, and/or depression requires inhibitory neurotransmitters to fill the synapses between the individual brain cells. Inhibitory neurotransmitters in the synapses reduce the transmittal of stress, anxiety, grief, and/or depression related messages from the limbic system to the cortex. With a reduction in such messages, a person feels better because the emotional responses associated with stress, anxiety, grief, and/or depression are dampened.

When the body experiences stress, anxiety, grief, and/or depression, the brain releases increased amounts of inhibitory neurotransmitters. That release frequently depletes stores of inhibitory neurotransmitters faster than the body can reproduce them. Furthermore, such stores of inhibitory neurotransmitters are often deficient due to an improper intake of the nutrients that produce them. Thus, the emotional responses associated with stress, anxiety, grief, and/or depression can be greatly magnified thereby creating an extremely unhealthy condition for the body.

The combination of GABA, glutamine, and glycine in the compositional blend replenishes deficiencies in inhibitory neurotransmitters created either through increased release or insufficient stores. The combination of GABA, glutamine, and glycine enters the brain through the bloodstream so that, when a person experiences stress, anxiety, grief, and/or depression, sufficient amounts of inhibitory neurotransmitters are present to reduce the transmittal of stress, anxiety, grief, and/or depression related messages from the limbic system to the cortex. Additionally, glycine calms aggression and manic episodes.

The compositional blend includes magnesium to relieve muscle contractions and/or spasms. The human body cannot store magnesium, and a person experiencing stress, anxiety, grief, and/or depression burns available magnesium at a high rate. Muscles require magnesium, and, when levels within the body becomes deficient, muscle contractions and/or spasms occur. The magnesium in the compositional blend therefore replenishes deficiencies to prevent associated muscle contractions and spasms.

The compositional blend includes passion flower to relieve nervousness, nervous tension, anxiety, and/or spasms. Passion flower is an herb that acts as a sedative or nervine for the human body to lessen the nervousness, nervous tension, anxiety, and/or spasms normally associated with stress, anxiety, grief, and/or depression.

The compositional blend includes primula officinalis to relieve nervous tension and/or insomnia. Primula officinalis is an herb that acts as a sedative or nervine for the human body to lessen the nervous tension and/or insomnia typically associated with stress, anxiety, grief, and/or depression.

The compositional blend includes vitamin B-6 (pyridoxine) to metabolize the amino acids GABA, glutamine, and glycine within the brain. Amino acids such as GABA, glutamine, and glycine will not metabolize to form inhibitory neurotransmitters within the brain without a vitamin cofactor. The vitamin B-6 in the compositional blend therefore provides the necessary vitamin cofactor required by the amino acids GABA, glutamine, and glycine.

Although the present invention has been described in terms of the foregoing embodiment, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing description, rather, it is defined only by the claims that follow.

I claim:

1. A composition for relieving stress, anxiety, grief, and depression, comprising: GABA, glutamine, glycine, magnesium, passion flower, primula officinalis, and vitamin B-6.

2. The composition according to claim 1 wherein GABA comprises from about 33.3% to about 43.0% total composition weight.

3. The composition according to claim 1 wherein glutamine comprises from about 11.4% to about 15.2% total composition weight.

4. The composition according to claim 1 wherein glycine comprises from about 7.6% to about 11.4% total composition weight.

5. The composition according to claim 1 wherein magnesium comprises from about 7.6% to about 11.4% total composition weight.

6. The composition according to claim 1 wherein passion flower comprises from about 12.4% to about 16.2% total composition weight.

7. The composition according to claim 1 wherein primula officinalis comprises from about 12.4% to about 16.2% total composition weight.

8. The composition according to claim 1 wherein vitamin B-6 comprises from about 0.7% to about 1.2% total composition weight.

9. A composition for relieving stress, anxiety, grief, and depression, comprising:

GABA from about 33.3% to about 43.0% total composition weight;

glutamine from about 11.4% to about 15.2% total composition weight;

glycine from about 7.6% to about 11.4% total composition weight;

magnesium from about 7.6% to about 11.4% total composition weight;

passion flower from about 12.4% to about 16.2% total composition weight;

primula officinalis from about 12.4% to about 16.2% total composition weight; and vitamin B-6 from about 0.7% to about 1.2% total composition weight.

10. A composition in capsule form for relieving stress, anxiety, grief, and depression wherein four capsules comprise:

800 mg of GABA;

280 mg of glutamine;

200 mg of glycine;

200 mg of magnesium;

300 mg of passion flower;

300 mg of primula officinalis; and 20 mg of vitamin B-6.

* * * * *